United States Patent
Wang et al.

(10) Patent No.: US 6,359,164 B1
(45) Date of Patent: Mar. 19, 2002

(54) PROCESS FOR THE PREPARATION OF CYCLOPROPYLACETYLENE

(76) Inventors: Zhe Wang, 67 Westwoods Blvd., Hockessin, DE (US) 19707; Joseph M. Fortunak, 19 Somerset La., Newark, DE (US) 19711

(*) Notice: Subject to any disclaimer, the term of this patent is extended or adjusted under 35 U.S.C. 154(b) by 0 days.

(21) Appl. No.: 09/408,132

(22) Filed: Sep. 30, 1999

Related U.S. Application Data
(60) Provisional application No. 60/102,643, filed on Oct. 1, 1998.

(51) Int. Cl.$^7$ .............. C07C 5/00; C07C 1/207; C07C 13/04; C07C 69/708; C07C 59/13; C07C 67/31; C07C 51/363
(52) U.S. Cl. .............. 558/371; 560/124; 562/506; 585/359; 585/534; 585/538
(58) Field of Search ................ 585/538, 534, 585/359; 560/124; 562/506; 558/371

(56) References Cited

U.S. PATENT DOCUMENTS

| | | | |
|---|---|---|---|
| 5,250,540 A | 10/1993 | Arlt et al. | 514/302 |
| 5,318,988 A | 6/1994 | Schohe-Loop et al. | 514/458 |
| 5,407,599 A | 4/1995 | De Maijere et al. | 252/299 |
| 5,468,882 A | 11/1995 | Schohe-Loop et al. | 549/407 |
| 5,663,467 A | 9/1997 | Thompson et al. | 585/359 |
| 6,028,237 A * | 2/2000 | Parsons | 585/359 |
| 6,049,019 A * | 4/2000 | Fortunak et al. | 585/538 |
| 6,207,864 B1 | 3/2001 | Henningsen et al. | 568/348 |

FOREIGN PATENT DOCUMENTS

| | | |
|---|---|---|
| EP | 0847974 | 6/1998 |
| WO | 96-22955 | 8/1996 |
| WO | 96-37457 | 11/1996 |

OTHER PUBLICATIONS

Craig et al., Angew. Chem. Int. Ed. Engl., (1969), 8(6), 429–437.
Schoberth and Hanack, Synthesis (1972), (12), 703.
Taguchi et al., J. Am. Chem. Soc., (1974), 96(9), 3010–3011.
Wong and Ho, Synthetic Communications, (1974), 4(1), 25–27.
Villieras et al., Synthesis, (1975), 458–461.
Tsuji et al., Chemistry Letters, (1979), 481–482.
Van Hijfte et al., Tetrahedron Letters, (1989), 30(28) 3655–3656.
Corey et al., Tetrahedron Letters, (1992), 33(24), 3435–3438.
Grandjean et al., Tetrahedron Letters, (1994), 35(21), 3529–3530.
Thompson et al., Tetrahedron Letters, (1995), 36(49), 8937–8940.
Ihara et al., Tetrahedron, (1995), 51(36), 9873–9890.
Bunnage and Nicolaou, Angew. Chem. Int. Ed. Engl., (1996), 35(10), 1110–1112.
Carl Bernard Ziegler, Jr., Syhthesis and Mechanistic Studies of Polyunsaturated Fatty Acid Hydroperoxides Involving a Novel . . . Ring., Ph.D. Dissertation, Duke University (1981), 139 pp.

* cited by examiner

*Primary Examiner*—Floyd D. Higel

(57) ABSTRACT

The present invention relates generally to novel methods for the preparation of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor with superior antiretroviral activity. In the process, for example, cyclopropane carboxaldehyde is alkylated to form 1,1,1-trichloro-2-cyclopropyl-ethanol; which in turn undergoes elimination to form 1,1-dichloro-2-cyclopropyl-ethene; which in turn undergoes elimination to form cyclopropyl acetylene.

22 Claims, No Drawings

PROCESS FOR THE PREPARATION OF CYCLOPROPYLACETYLENE

This application claims the benefit of U.S. Provisional Application No. 60/102,643, filed Oct. 1, 1998.

FIELD OF THE INVENTION

The present invention relates generally to novel methods for the preparation of cyclopropylacetylene which is an essential reagent in the asymmetric synthesis of (S)-6-chloro-4-cyclopropylethynyl-4-trifluoromethyl-1,4-dihydro-2H-3,1-benzoxazin-2-one; a useful human immunodeficiency virus (HIV) reverse transcriptase inhibitor with superior anti-retroviral activity. In the process, for example, cyclopropane carboxaldehyde is alkylated to form 1,1,1-trichloro-2-cyclopropyl-ethanol; which in turn undergoes elimination to form 1,1-dichloro-2-cyclopropyl-ethene; which in turn undergoes elimination to form cyclopropylacetylene.

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The (S)-6-chloro-4-cyclopropylethynyl-4-trifluoromethyl-1,4-dihydro-2H-3,1-benzoxazin-2-one of formula (VI):

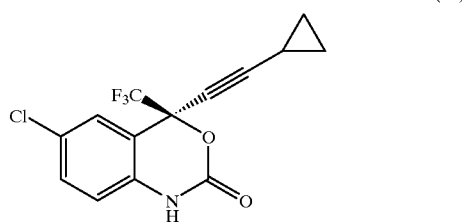

(VI)

generically known as efavirenz (SUSTIVA™), is not only a highly potent reverse transcriptase inhibitor, it is also efficacious against HIV reverse transcriptase resistance. Due to the importance of SUSTIVA™ as a reverse transcriptase inhibitor, economical and efficient synthetic processes for its production need to be developed.

Cyclopropylacetylene is an important reagent in the synthesis of compound (VI). Cyclopropylacetylene is also the most expensive raw material, of which availablity is difficult to obtain.

Thompson et al, Tetrahedron Letters 1995, 36, 937–940, describe the asymmetric synthesis of an enantiomeric benzoxazinone by a highly enantioselective acetylide addition followed by cyclization with a condensing agent to form the benzoxazinone shown below. As a reagent the cyclopropyl acetylene was synthesized in a 65% yield by cyclization of 5-chloropentyne with n-butyllithium at 0°–80° C. in cyclohexane followed by quenching with ammonium chloride. The process generates a low yield of cyclopropylacetylene which is not feasible for the large commercial process of a difficult to handle reagent.

Thompson et al, PCT International Patent Application Number WO 9622955 A1 describe an improved synthesis of cyclopropylacetylene useful in the synthesis of (S)-6-chloro-4-cyclopropylethynyl-4-trifluoromethyl-1,4-dihydro-2H-3,1-benzoxazin-2-one. Application WO 9622955 A1 discloses methods which continue to be inefficient in the overall synthesis on a kilogram scale for which this invention makes significant improvements.

The chemical literature shows the majority of the cyclopropylacetylene preparations involve the conversion of cyclopropylmethyl ketone to cyclopropylacetylene via the following chemical scheme. The method will produce cyclopropylacetylene on small scale, <1 kilogram, but is not amenable for bulk production, thus an alternative was developed.

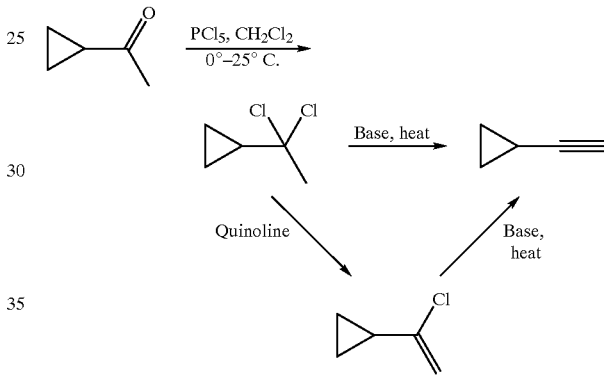

In addition to conversion of cyclopropylmethyl ketone to cyclopropylacetylene, Corey-Fuchs, Horner-Emomons and Gillbert-Seyferth reactions are the most frequently used methods for the conversion of aldehydes to terminal alkynes via a one-carbon homologation. The requirements of phosphorous reagents to promote these reactions, however, limit their industrial attractiveness and efficiency of these applications due to the problems of toxicity and volume of waste streams generated.

The above methods for, the synthesis of cyclopropylacetylene use combinations of toxic, difficult to handle reagents, relatively expensive materials, incomplete conversions and/or low yields which render the overall synthesis inefficient and yield cyclopropylacetylene of lower purity. Thus, it is desirable to discover new synthetic routes to cyclopropylacetylene on a large scale which improve upon these limitations and provide high yields of desired cyclopropylacetylene.

The present invention discloses a novel, scalable, and efficient process for the preparation of substituted acetylenes, more specifically cyclopropylacetylene, via a one carbon homologation of substituted aldehydes. Improvements over previously disclosed preparations of cyclopropyl acetylene are in the low economic price and availability of the starting materials; the convenience and high yields for the chemistry; the efficiency of the process; the ease in handling of the 1,1-dichlorovinyl intermediates; and the ability to store without degradation the 1,1- dichlorovinyl intermediates. The invention provides novel chemistry for the production of cyclopropylacetylene from cyclopropane carboxaldehyde. The process provides a high yield for the convenient reaction of cyclopropane carboxaldehyde with trichloroacetic acid followed by zinc to give 1,1-dichloro-2-cyclopropylethene. The intermediate, 1,1-dichloro-2-cyclopropylethene, is a very stable liquid, easily purified by distillation, and produced in high yield. The subsequent dehalogenation of 1,1-dichloro-2-cyclopropylethene to cyclopropylacetylene proceeds in high yields and with suitable purities so that the cyclopropyl acetylene produced and isolated can be stored or used as a solution in an inert solvent.

None of the above-cited references describe the methods of the present invention for the synthesis of cyclopropyl acetylene. None of the above-cited references describe the unexpected benefit that 2-substituted 1,1-dichloroethenes contribute to the overall efficiency of the invention.

SUMMARY OF THE INVENTION

The present invention concerns an improved process suitable for the large scale preparation of cyclopropyl acetylene. In the process, cyclopropane carboxaldehyde is condensed with an alkylating/halogenating agent, such as trichloroacetic acid, to form 1,1,1-trichloro-2-cyclopropylethanol in situ; 1,1,1-trichloro-2-cyclopropylethanol is optionally protected in situ to form 1,1,1-trichloro-2-cyclopropyl-2-ethanylacetate; the 1,1,1-trichloro-2-cyclopropylethanol and/or 1,1,1-trichloro-2-cyclopropyl-2-ethanylacetate is reduced to form 1,1-trichloro-2-cyclopropyl ethene, which is easily isolated; and 1,1-trichloro-2-cyclopropylethene is dehalogenated to form cyclopropyl acetylene. This improvement provides for high conversion of inexpensive, readily available starting materials into cyclopropyl acetylene, with high overall yields, easily handled intermediates, and can be conducted on an industrial scale.

DETAILED DESCRIPTION OF THE INVENTION

In a first embodiment, the present invention provides a process for the preparation of a compound of formula (III);

(III)

wherein:
$R^1$ is selected from:
$C_{1-8}$ alkyl substituted with 0–3 $R^4$,
$C_{3-10}$ cycloalkyl substituted with 0–2 $R^5$, and
aryl substituted with 0–2 $R^6$;
$R^4$, at each occurrence, is selected from methyl, ethyl, propyl, butyl, $OR^7$, $NR^7R^{7a}$, phenyl, and cyclopropyl;
$R^5$, at each occurrence, is selected from D, methyl, ethyl, propyl, methoxy, ethoxy, and propoxy;
$R^6$, at each occurrence, is selected from methyl, ethyl, propyl, methoxy, ethoxy, propoxy, F, Cl, B, I, CN, and $NR^7R^{7a}$;
$R^7$ and $R^{7a}$ are independently selected from methyl, ethyl, propyl, and butyl;
said process comprising:
(1a) contacting an aldehyde of formula $R^1$-CHO with trichloroacetic acid or tribromoacetic acid, in the presence of a base catalyst;

(1b) contacting the solution of (1a) with zinc in the presence of a suitable acid to form a compound of formula (II);

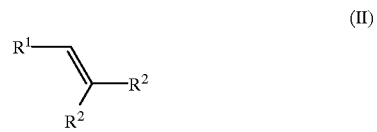
(II)

wherein $R^2$ is Cl or Br; and
(2) contacting a compound of formula (II) with a strong base to form a compound of formula (III).

In a preferred embodiment, the present invention provides a process for the preparation of cyclopropylacetylene comprising:
(1a) contacting cyclopropane carboxaldehyde with trichloroacetic acid in the presence of a base catalyst;
(1b) contacting the solution of (1a) with zinc in the presence of a suitable acid to form 1,1-dichloro-2-cyclopropylethene; and
(2) contacting 1,1-dichloro-2-cyclopropylethene with a strong base to form cyclopropyl acetylene.

In a further preferred embodiment the base catalyst comprises sodium trichloroacetate.

In a further preferred embodiment the suitable acid comprises acetic acid.

In a further preferred embodiment the strong base comprises methyl lithium or sodium amide.

In a further preferred embodiment the preparation of cyclopropylacetylene comprises:
(1a) contacting cyclopropane carboxaldehyde with trichloroacetic acid in the presence of a sodium trichloroacetate;
(1b) contacting the solution of (1a) with zinc in the presence of acetic acid to form 1,1-dichloro-2-cyclopropylethene; and
(2) contacting 1,1-dichloro-2-cyclopropylethene with methyl lithium to form cyclopropyl acetylene.

In a more preferred embodiment a process for the preparation of 1,1-dichloro-2-cyclopropylethene comprises:
(1a) contacting cyclopropane carboxaldehyde with trichloroacetic acid in the presence of a base catalyst; and
(1b) contacting the solution of (1a) with zinc in the presence of a suitable acid to form 1,1-dichloro-2-cyclopropylethene.

In a further more preferred embodiment the base catalyst comprises sodium trichloroacetate.

In a further more preferred embodiment the suitable acid comprises acetic acid.

In a further more preferred embodiment the process for the preparation of 1,1-dichloro-2-cyclopropylethene comprises:
(1a) contacting cyclopropane carboxaldehyde with trichloroacetic acid in the presence of a sodium trichloroacetate; and
(1b) contacting the solution of (1a) with zinc in the presence of acetic acid to form 1,1-dichloro-2-cyclopropylethene.

In a second embodiment, the present invention provides a process for the preparation of a compound of formula (III);

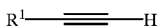

(III)

wherein:
R¹ is selected from:
C$_{1-8}$ alkyl substituted with 0–3 R⁴,
C$_{3-10}$ cycloalkyl substituted with 0–2 R⁵, and
aryl substituted with 0–2 R⁶;
R⁴, at each occurrence, is selected from methyl, ethyl, propyl, butyl, OR⁷, NR⁷R⁷ᵃ, phenyl, and cyclopropyl;
R⁵, at each occurrence, is selected from D, methyl, ethyl, propyl, methoxy, ethoxy, and propoxy;
R⁶, at each occurrence, is selected from methyl, ethyl, propyl, methoxy, ethoxy, propoxy, F, Cl, B, I, CN, and NR⁷R⁷ᵃ;
R⁷ and R⁷ᵃ are independently selected from methyl, ethyl, propyl, and butyl;
said process comprising:
(1a) contacting an aldehyde of formula R¹-CHO with trichloroacetic acid or tribromoacetic acid, in the presence of a base catalyst;
(1b) contacting the solution of (1a) with a hydroxy group protecting agent;
(1c) contacting the solution of (1b) with zinc in the presence of a suitable acid to form a compound of formula (II);

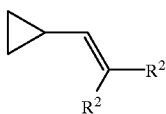

(II)

wherein R² is Cl or Br; and
(2) contacting a compound of formula (II) with a strong base to form a compound of formula (III).

In a preferred embodiment, the present invention provides a process for the preparation of cyclopropylacetylene comprising:
(1a) contacting cyclopropane carboxaldehyde with trichloroacetic acid in the presence of a base catalyst;
(1b) contacting the solution of (1a) with a hydroxy group protecting agent;
(1c) contacting the solution of (1b) with zinc in the presence of a suitable acid to form 1,1-dichloro-2-cyclopropylethene; and
(2) contacting 1,1-dichloro-2-cyclopropylethene with a strong base to form cyclopropyl acetylene.

In a further preferred embodiment the base catalyst comprises sodium trichloroacetate.

In a further preferred embodiment the hydroxy group protecting agent comprises acetic anhydride.

In a further preferred embodiment the suitable acid comprises acetic acid.

In a further preferred embodiment the strong base comprises methyl lithium or sodium amide.

In a further preferred embodiment the process for the preparation of cyclopropylacetylene comprises:
(1a) contacting cyclopropane carboxaldehyde with trichloroacetic acid in the presence of sodium trichloroacetate;
(1b) contacting the solution of (1a) with acetic anhydride;
(1c) contacting the solution of (1b) with zinc in the presence of acetic acid to form 1,1-dichloro-2-cyclopropylethene; and
(2) contacting 1,1-dichloro-2-cyclopropylethene with a methyl lithium to form cyclopropyl acetylene.

In a more preferred embodiment, the present invention provides a process for the preparation of 1,1-dichloro-2-cyclopropylethene comprising:
(1a) contacting cyclopropane carboxaldehyde with trichloroacetic acid in the presence of a base catalyst;
(1b) contacting the solution of (1a) with a hydroxy group protecting agent; and
(1c) contacting the solution of (1b) with zinc in the presence of a suitable acid to form 1,1-dichloro-2-cyclopropylethene.

In a further more preferred embodiment the base catalyst comprises sodium trichloroacetate.

In a further more preferred embodiment the hydroxy group protecting agent comprises acetic anhydride.

In a further more preferred embodiment the suitable acid comprises acetic acid.

In a further more preferred embodiment the process for the preparation of 1,1-dichloro-2-cyclopropylethene comprises:
(1a) contacting cyclopropane carboxaldehyde with trichloroacetic acid in the presence of sodium trichloroacetate;
(1b) contacting the solution of (1a) with acetic anhydride; and
(1c) contacting the solution of (1b) with zinc in the presence of acetic acid to form 1,1-dichloro-2-cyclopropylethene.

The processes of the present invention are useful for the preparation cyclopropylacetylene, an essential intermediate in the synthesis of (S)-6-chloro-4-cyclopropylethynyl-4-trifluoromethyl-1,4-dihydro-2H-3,1-benzoxazin-2-one, which is useful as a human immunodeficiency virus (HIV) reverse transcriptase inhibitor, and compounds which are useful intermediates in the synthesis of (S)-6-chloro-4-cyclopropylethynyl-4-trifluoromethyl-1,4-dihydro-2H-3,1-benzoxazin-2-one. Such HIV reverse transcriptase inhibitors are useful for the inhibition of HIV and the treatment of HIV infection. Such HIV reverse transcriptase inhibitors are useful for the inhibition of HIV in an ex vivo sample containing HIV or expected to be exposed to HIV. Thus, such HIV reverse transcriptase inhibitors may be used to inhibit HIV present in a body fluid sample (for example, a body fluid or semen sample) which contains or is suspected to contain or be exposed to HIV. Such HIV reverse transcriptase inhibitors are also useful as standards or reference compounds for use in tests or assays for determining the ability of an agent to inhibit viral replication and/or HIV reverse transcriptase, for example in a pharmaceutical research program. Thus, such HIV reverse transcriptase inhibitors may be used as a control or reference compound in such assays and as a quality control standard.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature, unless the purpose of the solvent is to quench the reaction. A given reaction may be carried out in one solvent or a mixture of more than one solvent. Depending on the particular reaction step, suitable solvents for a particular reaction step may be selected independent of any other reaction step.

Suitable amide solvents include, but are not limited to, dimethylformamide, dimethylacetamide, dimethylpropionamide, and 1-methyl-2-pyrrolidinone.

Suitable halogenated solvents include chlorobenzene, dichloromethane, chloroform, carbon tetrachloride, dichlorobenzene, dichloroethane, and trichloroethane.

Suitable ether solvents include: tetrahydrofuran, diethyl ether, ethylene glycol dimethyl ether, ethylene glycol diethyl ether, diethylene glycol dimethyl ether, diethylene glycol diethyl ether, triethylene glycol dimethyl ether, anisole, or t-butylmethyl ether.

Suitable hydrocarbon or aromatic solvents include: benzene, cyclohexane, pentane, hexane, toluene, cycloheptane, methylcyclohexane, heptane, ethylbenzene, m-xylene, o-xylene, p-xylene, octane, indane, nonane, naphthalene and mesitylene(s).

As used herein, the term "base catalyst" refers to any agent which catalyzes the alkylation of cyclopropyl carboxaldehyde by the anion of trihalomethane thus effecting the formation of a halogenated cyclopropyl carbinol. Examples of base catalysts, depending on the source of anion, include, but are not limited to, sodium trihaloacetate, sodium acetate, sodium hydride, sodium hydroxide, sodium methoxide, sodium ethoxide, potassium t-butoxide, lithium amide, lithium dialkyl amides, lithium diisopropyl amide (LDA), KHMDA, and LiHMDA.

As used herein, the term "hydroxy group protecting agent" or "alcohol protecting agent" refers to any reagent suitable to convert a hydroxyl group to a leaving group, the presence of which in the reaction converts the OH of carbinol of formula 2a (in Scheme 1) into a leaving group. A variety of such reagents will be appreciated by one of skill in the art of organic synthesis. Such reagents may be selected from, for example but not limited to, reagents of formula $ClSO_2X$, such as benzenesulfonyl chloride, toluenesulfonyl chloride, dimethylbenzenesulfonyl chloride, trimethylbenzene sulfonyl chloride, chlorobenzenesulfonyl chloride, dichlorobenzenesulfonyl chloride, trichlorobenzenesulfonyl chloride, methanesulfonyl chloride, ethanesulfonyl chloride, propanesulfonyl chloride, butanesulfonyl chloride. Such reagents may also be selected from, for example but not limited to, reagents of anhydrides, such as acetyl anhydride, tosyl anhydride, and mesylanhydride. Such reagents may also be selected from, for example but not limited to, reagents of acid chlorides, such as acetyl chloride.

As used herein, the term "hydroxy protecting group" or "OH protecting group" refers to any group derived from the "hydroxy group protecting agent" which replaces the proton of the OH of carbinol of formula 2a after reaction of the carbinol with a "hydroxy group protecting agent". A variety of such reagents will be appreciated by one of skill in the art of organic synthesis. Such reagents may be selected from, for example but not limited to, radicals of formula $—SO_2X$, such as benzenesulfonyl, toluenesulfonyl, dimethylbenzenesulfonyl, trimethylbenzene sulfonyl, chlorobenzenesulfonyl, dichlorobenzenesulfonyl, trichlorobenzenesulfonyl, methanesulfonyl, ethanesulfonyl, propanesulfonyl, butanesulfonyl. Such reagents may also be selected from, for example but not limited to, radicals derived from anhydrides, such as acetyl, tosyl, and mesyl. Such reagents may also be selected from, for example but not limited to, radicals derived from acid chlorides, such as acetyl.

As used in step (1) for the reaction of zinc with 2a or 2b, the term "suitable acid" or "acid" refers to organic acids, preferably alkyl acids, having one to six carbons. A suitable acid is either liquid at room temperature and soluble in the reaction solvent or a solid which is soluble in the reaction solvent. Examples of a suitable acid include, but are not limited to, acetic acid, propionic acid, butyric acid, isobutyric acid, valeric acid, isovaleric acid, and hexanoic acid.

As used herein, the term "strong base" refers to any organometallic base the presence of which in the reaction facilitates the synthesis of cyclopropyl acetylene from dihalovinyl compounds of formula 2. Suitable strong bases may be selected by one of skill in the art of organic synthesis. Suitable strong bases include, but are not limited to, metal amides, alkyl lithiums, and grignard reagents. Such strong bases include sodium amide, potassium amide, lithium amide, lithium diisopropylamide, methyllithium, butyllithium, hexyllithium, phenyllithium, and butyl magnesium chloride. Examples of suitable strong bases are sodium amide, sodium methoxide, potassium t-butoxide, sodium butoxide, potassium and sodium t-amyloxide, potassium hydroxide, sodium hydroxide, methyllithium, butyllithium, hexyllithium, phenyllithium.

The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

Synthesis

It is the object of the present invention to provide a novel and improved process for the synthesis of substituted acetylenes, more specifically cyclopropylacetylene, which are useful in the synthesis of HIV reverse transcriptase inhibitors, such as substituted benzoxizinones. The methods of the present invention, by way of example and without limitation, may be further understood by reference to Scheme 1. Scheme 1 details the improved general synthetic method for synthesis of cyclopropylacetylene from cyclopropyl carboxaldehyde. Cyclopropylcarboxaldehyde is alkylated by an in situ generated trihalomethyl anion followed by elimination to form a 1,1-dichloroolefin; the olefin undergoes further elimination in a second step to produce cyclopropyl acetylene in quantitative yield.

Although Scheme 1 demonstrates cyclopropyl substituted acetylene synthesis, it is an object of the present invention that substitutents other than cyclopropyl can be use in this invention. Similarly, the trihalomethyl anion can be tribromomethyl.

Scheme 1

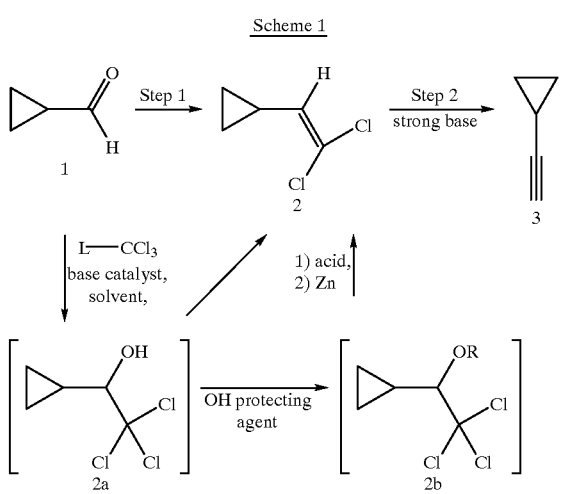

Step 1. Combined in situ alkylation and elimination of cyclopropyl carboxaldehyde to form cyclopropylvinyl dichloride This step is conducted by reacting cyclopropyl carboxaldehyde in a suitable nonaqueous solvent at a suitable temperature with trichloroacetic acid in the presence of a suitable base catalyst to form cyclopropyltrichlorocarbinol of formula 2a in situ. Upon formation of cyclopropyltrichlorocarbinol in situ the mixture is diluted with a suitable acid and subsequently reacted with zinc to form cyclopropyl vinyl dichloride. By way of general guidance, a reaction vessel is charged with a solution of trichloroacetic acid (about 1.2 to about 2.0 equivalents, preferably 1.5 eq) in a nonaqueous solvent. The aldehyde (about 1 eq.) is added into the solution preferably with a continues $N_2$ flow. To this stirred solution is added a base catalyst (about 1.2 to about 2.0 equivalents, preferably 1.5 eq) portionwise. The $N_2$ flow, if used, is stopped and the heterogeneous mixture is stirred at room temperature for preferably 1 to 5 hours, more preferably about 3 hours, with continuous evolution of $CO_2$. Generally, the reaction can be monitored by $^1$H-NMR indicating the reaction completion by disappearance of the aldehyde proton signal. The mixture is diluted with a suitable acid and cooled to a suitable temperature below room temperature. Nitrogen flow, if previously discontinued, is preferably turned back on and about two equivalents of zinc is added, preferably in one portion. Because the elimination reaction due to the presence of zinc is exothermic, the internal temperature increases. The solution is stirred at a temperature above room temperature, preferably about 60° C. for about 1 h after which the mixture is cooled to room temperature. The product, 2, is isolated by standard methods of work up, preferably by distillation. Examples of standard work up are shown in Examples 1 and 2.

It is preferred that the reaction vessel is dried (for example by heat-air-gun or oven) and equipped with mechanical stirrer, nitrogen inlet and an outlet connected to a bubbler.

Suitable nonaqueous solvents are any amide solvents and sulfoxide solvents in which the aldehyde is soluble. These include, but are not limited to, dimethylformamide, dimethylsulfoxide, and 1-methyl-2-pyrrolidinone. Preferred nonaqueous solvent is dimethylformamide.

The concentration of aldehyde in the solvent may range from about 0.5 molar to about 3.0 molar. Preferred is 0.5 molar to 2.0 molar; more preferred is about 1.5 molar.

Base catalysts for the alkylation of the aldehyde by a trihaloacetic acid include, but are not limited to, sodium trichloroacetate, sodium hydride, sodium hydroxide, and sodium methoxide. Preferred is sodium trichloroacetate. It is understood that the concentration of base catalyst is about equivalent to the concentration of the trichloroacetic acid.

It is understood that tribromoacetic acid, or any other analogue, can be substituted for trichloroacetic acid in this reaction. It is also understood that the reaction is generally applicable to a large scope of substitutents in the cyclopropyl position as exemplified below.

Suitable temperature for the alkylation reaction ranges from the freezing point to refluxing temperature of the nonaqueous solvent, a condition readily determined by one skilled in the art of organic synthesis. It is preferred, for handling purposes, to run the reaction with an internal temperature below 35° C. during addition. It is more preferred to run the reaction at room temperature.

Suitable temperature for the addition of zinc to form the vinyldichloride by elimination ranges from the freezing point to about room temperature; more preferably about −10° C. to about 10° C., even more preferably about 0° C., a condition readily determined by one skilled in the art of organic synthesis. After addition of the strong base it is preferred, for handling purposes, to run the reaction with an internal temperature below the boiling point of vinyl dichloride being formed, preferably about room temperature to just below the boiling point of vinyl dichloride being formed. In the example of cyclopropyl vinyl dichloride the preferred temperature is room temperature to about 60° C., more preferably about 40° C. to about 60° C. It is most preferred to run the reaction at about 60° C.

For addition of zinc to the trichlorocarbinol preferred suitable acids are acetic acid, propionic acid and butyric acid. More preferred is acetic acid.

It is understood that one skilled in the art can determine the preferred reaction time of Step 1 as dependent on nonaqueous solvent, temperature, base catalyst and concentration of reagents. Generally, the reaction time is about 1 to about 16 hours. The prefered reaction time is about 1 to about 8 hours.

Alternatively, as illustrated in Scheme 1 the OH group of the trichlorocarbinol species, 2a, may be protected in situ with an alcohol protecting group to form 2b which in turn readily undergoes elimination in the presence of zinc under the conditions previously stated to form the vinyl dichloride of formula 2.

This additional modification comprises the protection of the carbinol OH with an alcohol protecting group by contacting the in situ carbinol 2a with an alcohol protecting agent to form a compound of formula 2b in situ. By way of general guidance, one equivalent of trichlorocarbinol as generated previously in situ is contacted with about 1 to about 3 equivalents, preferably 2 equivalents, of an alcohol protecting agent at a suitable temperature. The suitable temperature is about 0° C. to room temperature, preferably about 0° C. to 10° C. This solution is allowed to warm to room temperature after which it is stirred for about one to four, preferably about 1 to about 2 hours. After this period of time, generally, a proton NMR indicates completion of the reaction. The product, 2b, is subsequently reacted with zinc as previously described.

Alcohol protecting agents suitable for this step are sulfonyl chlorides, sulfonyl anhydrides, acid chlorides and anhydrides. Preferred alcohol protecting agents are toluenesulfonyl chloride, toluenesulfonyl anhydride, methylsulfonyl chloride, methylsulfonyl anhydride, acetyl chloride and acetyl anhydride. More preferred is acetyl chloride and acetyl anhydride. Most preferred is acetyl anhydride.

The concentration of carbinol in the solvent may range from about 0.5 molar to about 5.0 molar. Preferred is 0.5 molar to 2.0 molar; more preferred is 1.0 molar.

It is understood that the reaction is generally applicable to a large scope of substitutents in the cyclopropyl position.

Step 2: Elimination: Preparation of cyclopropylacetylene

This step comprises an elimination by dehalogenation of cyclopropylvinyldichloride, 2, to form cyclopropylacetylene, 3. By way of general guidance, one equivalent of cyclopropylvinyldichloride (2) is dissolved in a suitable solvent. To this solution, while stirring at a suitable temperature, is added about 1 to about 3 equivalents, more preferably about 1.2 to about 2.2 equivalents, even more preferably about 1.5 to about 2 equivalents of a strong base, preferably dropwise, preferably by additional funnel. After addition is complete, the reaction mixture is slowly warmed to a temperature below the boiling point of alkyne, preferably about 0° C. to room temperature, more preferably about 0° C. A simple way to monitor the reaction progress is by $^1$H-NMR or GC. The alkyne product, 3, is provided by work up. Examples of standard work up are shown in Examples 1 and 2. Crude alkyne is obtained in excellent yield. Simple distillation is prefered to purify the alkyne.

It is preferred that the reaction vessel is dried (for example by heat-air-gun or oven) and equipped with mechanical stirrer, additional funnel, nitrogen inlet and an outlet connected to a bubbler.

Suitable nonaqueous solvents for step (2) are nonprotic solvents such as nonhalogenated solvents, ether solvents, hydrocarbon or aromatic solvents, including acetonitrile and dimethylsulfoxide. Preferred solvents when organometallic reagents are employed as the strong base include tetrahydrofuran, diethylether, dimethylsulfoxide, 1,4-dioxane, acetonitrile, N-methylpyrolidinone, heptane, hexanes, and toluene. Generally, more preferred is tetrahydrofuran. When sodium amide is the strong base DMSO is more preferred. Additionally, it is preferred that the solvent is dry.

Suitable temperature for the elimination reaction ranges from about –30° C. to about 10° C. for the addition of the strong base, more preferably about –30° C. to about 0° C., even more preferably about about –30° C. to about –20° C., a condition readily determined by one skilled in the art of organic synthesis. After addition of the strong base it is preferred, for handling purposes, to run the reaction with an internal temperature below the boiling point of alkyne being formed, preferably about 0° C. to room temperature, more preferably about 0° C.

Strong bases for step (2) are organometallic bases such as metal amides, alkyl lithiums, and grignard reagents. Such strong bases include sodium amide, potassium amide, lithium amide, lithium diisopropylamide, methyllithium, butyllithium, hexyllithium, phenyllithium, and butyl magnesium chloride. Prefered bases are sodium amide, potassium amide, lithium amide, and methyllithium; more prefered is sodium amide and methyllithium.

The elimination can also be carried out by substituting suitable metals for the "strong base". The suitable metal can form a vinyl grignard species which in turn then forms the desired alkyne. An example of such suitable metals is magnesium.

The concentration of 1,1-dichlorovinyl species 2 in the solvent may range from about 0.5 molar to about 5.0 molar. Preferred is 0.5 molar to 3.0 molar; more preferred is 1.0 to 2.0 molar.

It is understood that the reaction is generally applicable to a large scope of substitutents in the cyclopropyl position as exemplified below.

The following examples are meant to be illustrative of the present invention. These examples are presented to exemplify the invention and are not to be construed as limiting the invention's scope.

EXAMPLE 1

General procedure for preparation of vinyl dichlorides: A 3 L, three neck rounded-bottom flask equipped with mechanical stirrer, nitrogen inlet and outlet connected to a bubbler, is charged with a solution of trichloroacetic acid (1.5 mols, 1.5 eq) in DMF (700 mL). The aldehyde (1 mol, 1 eq.) is then added with a continuos $N_2$ flow To this stirred solution is added sodium trichloroacetate (1.5 mols, 1.5 eq.) portionwise, keeping the internal temperature below 35° C. during addition. The $N_2$ flow is stopped and the heterogeneous mixture is stirred at room temperature for 3 hours. A strong evolution of $CO_2$ is observed. The mixture is allowed to warm to room temperature and stirred for an additional hour. After this period of time $^1$H-NMR showed the acetate intermediate. The thick mixture is diluted with acetic acid (400 mL) and cooled to 0° C. Nitrogen flow is back on and zinc (0.8 mols, 2 eq) is added in one portion. CAUTION, The reaction is exothermically self-initiated. The internal temperature increase to about 40° C. The solution is stirred at 60° C. for 1 h and then it is cooled to room temperature. Water (300 mL) is added and then extracted with hexane (3×500 mL). The combined organic phases are washed with water (500 mL) and a saturated aqueous solution of sodium chloride (500 mL). The organic phase is dried over $MgSO_4$ anhydrous, filtered and concentrated by rotary evaporation. The crude 1,1-dichloroolefin is obtained in relative good purity but it can be purified by flash chromatography or distillation.

General procedure for preparation of acetylene: In a dried, 100 mL, three neck round-bottomed flask equipped with a magnetic stirrer, additional funnel and a nitrogen inlet is dissolved the 1,1-dichloroolefine (29 mmols, 1 eq) in dried THF (40 mL). To this stirred solution at –30° C. is added MeLi (1.4 M in ether, 32 mmols, 1.2 eq) dropwise via additional funnel. After addition is completed, the reaction mixture is allowed to slowly warm to 0° C. in a period of one hour. A simple way to monitor the reaction progress is by $^1$H-NMR. The reaction is quenched with saturated aqueous solution of ammonium chloride (50 mL) and diluted with t-butyl methyl ether (100 mL). The aqueous phase is extracted with t-butyl methyl ether (3×50 mL). The combine organic phase is washed with brine (50 mL) and dried over $MgSO_4$ anhydrous. After filtration and condensation crude acetylene is obtained in excellent yield. A simple distillation is recommended to purify the acetylene. The acetylene derivatives can characterized by comparison with commercially available authentic samples.

EXAMPLE 2

Preparation of Cyclopropylacetylene

Step 1: 1,1-dichloro-2-cyclopropylethene

This preparation is a typical example of this procedure: To a stirred solution of trichloroacetic acid (105 g, 0.642 mols), cyclopropyl carboxaldehyde (30 g, 0.428 mols) in DMF (300 mL) at 25° C. was added sodium trichloroacetate (119 g, 0.642 mols) in portions. The internal temperature was kept below 35° C. After addition was completed, the mixture was stirred at room temperature for 4 hours with continues evolution of $CO_2$. The reaction was monitored by $^1$H-NMR following the change of aldehyde proton signal. After this period of time, a very dark solution was observed and the reaction was completed. The solution was cooled to 5° C. and acetic anhydride (80.77 mL, 0.856 mols, 2 eq.) was carefully added. Strong $CO_2$ evolution was observed. The mixture was allowed to warm to room temperature and stirred for an additional hour. After this period of time $^1$H-NMR has shown the acetate intermediate. The thick mixture was diluted with acetic acid (400 mL) and cooled to 0° C. Nitrogen flow was back on and zinc (55.9 g, 0.856 mols, 2 eq) was added in one portion. CAUTION, The reaction is exothermically self-initiated. The internal temperature increase to about 40° C. The solution was stirred for 1 h at 60° C. and then it was cooled to room temperature. Water (300 mL) was added and then extracted with hexane (3×500 mL). The combined organic phases were washed with water (500 mL) and a saturated aqueous solution of sodium chloride (500 mL). The organic phase was dried over $MgSO_4$ anhydrous, filtered and concentrated by rotary evaporation. The crude 1,1-dichloro-2-cyclopropylethylene was obtained in relative good purity. Purification by flash chromatography (hex./EtOAc, 9:1) or distillation (b.p.= 47–51° C./2 torr) could be made. By this procedure 44.07 g (88%) of distilled material were obtained. $^1$H-NMR $\delta(CDCl_3)$: 0.52 (m, 2H), 0.87 (m, 2H), 1.61–1.73 (m, 1H), 5.25 (d, J=10.2 Hz, 1H). $^{13}$C-NMR $\delta(CDCl_3)$: 4.05, 5.32, 12.2, 72.02, 87.95 ppm. MS(CI/NH$_3$) (M+1): 139.

Step 2: cyclopropylacetylene (CPA)

This preparation is a typical example of this procedure: To a stirred solution of 1,1-dichloro-2-cyclopropylethylene (29.10 mmol) in dried THF (40 mL) at −30° C. was added MeLi (1.4 M in ether, 43.6 mmol, 1.5 eq.) dropwise via additional funnel. After the addition was completed, the solution was allowed to slowly warm to 0° C. in one hour period. At this time, TLC (hexane/ethyl acetate, 4:1) indicated no starting material left. The reaction was quenched with saturated aqueous solution of ammonium chloride (50 mL) and diluted with dodecane (100 mL). The aqueous phase was extracted with dodecane (2×50 mL). The combine organic phase was washed with brine (50 mL) and dried over $MgSO_4$ anhydrous. After filtration a 95% solution yield of CPA in THF/dodecane (1:6) was obtained. Neat CPA can be distilled by using fractional distillation at atmosphere pressure (b.p. 54–56° C.) and condensing it in a $CO_2$/acetone trap, which afford 1.71 g (89%) of neat CPA.

EXAMPLE 3

Preparation of 3,3-dimethyl-1-butyne

The title compound was prepared according to Scheme 2 using the procedures of Example 1 and/or 2 starting from trimethylacetaldehyde. The title product was compared to an authentic reference, the yield is listed in Table 1.

Intermediate; 1,1-dichloro-3,3-dimethyl-1-butene

Yield: 92%. b.p. 39°–41° C./10 mmHg. $^1$H-NMR $\delta(CDCl_3)$: 1.17 (s, 9H), 5.91 (s, 1H). $^{13}$C-NMR $\delta(CDCl_3)$: 28.22 (tert-butyl, 3C), 37.82, 87.88 ppm. MS(CI/NH$_3$) (M+1): 154

EXAMPLE 4

Preparation of Cyclohexylacetylene

The title compound was prepared according to Scheme 2 using the procedures of Example 1 and/or 2 starting from cyclohexanecarboxaldehyde. The title product was compared to an authentic reference, the yield is listed in Table 1.

Intermediate; 1,1-dichloro-2-cyclohexylethene

Yield 88%. b.p.:49°–52° C./10 mmHg. $^1$H-NMR $\delta(CDCl_3)$: 1.05–1.40 (m, 5H), 1.65–1.80 (m, 5H), 1.95 (m, 1H), 5.85 (d, J=7.2 Hz). $^{13}$C-NMR $\delta(CDCl_3)$: 21.80, 25.70, 25.87, 26.02, 28.00, 29.85, 39.85, 88.80 ppm. MS(CI/NH$_3$) (M+1): 180

EXAMPLE 5

Preparation of Phenylacetylene

The title compound was prepared according to Scheme 2 using the procedures of Example 1 and/or 2 starting from benzaldehyde The title product was compared to an authentic reference, the yield is listed in Table 1.

Intermediate; 1,1-dichloro-2-phenylethene

Yield: 86%. b.p.:75°–80° C./10 mmHg. $^1$H-NMR $\delta(CDCl_3)$: 6.92 (s, 1H), 7.27–7.57 (m, 3H), 7.60 (m, 2H). $^{13}$C-NMP $\delta(CDCl_3)$: 121.1, 126.0, 128.0 (5C), 133.2 ppm. MS(CI/NH$_3$) (M+l): 173

EXAMPLE 6

Preparation of 4-methyl-1-pentyne

The title compound was prepared according to Scheme 2 using the procedures of Example 1 and/or 2 starting from isovaleraldehyde. The title product was compared to an authentic reference, the yield is listed in Table 1.

Intermediate; 1,1-dichloro-3-methyl-1-pentene

Yield: 92%. b.p.:55°–57° C. /10 mmHg. $^1$H-NMR $\delta(CDCl_3)$: 0.92 (d, 3H), 0.95 (d, 3H), 1.71 (m, 1H), 2.15 (m, 2H), 5.84 (t, 1H). $^{13}$C-NMR $\delta(CDCl_3)$: 21.00, 28.00, 129.0 ppm. MS(CI/NH3) (M+1): 173

EXAMPLE 7

Preparation of 4-phenyl-1-butyne

The title compound was prepared according to Scheme 2 using the procedures of Example 1 and/or 2 starting from 3-phenylpropionaldehyde. The title product was compared to an authentic reference, the yield is listed in Table 1.

Intermediate; 1,1-dichloro-4-phenyl-1-butene

Yield: 85%. $^1$H-NMR $\delta(CDCl_3)$: 2.18–2.30 (m, 2H), 2.47–2.73 (m, 2H), 6.85 (t, 1H), 7.17–7.21 (m, 3H), 7.23–7.30 (m, 2H). $^{13}$C-NMR $\delta(CDCl_3)$: 31.57, 34.15, 126.3, 128.4, 128.6, 140.1 ppm. MS(CI/NH$_3$) (M+1): 202.

EXAMPLE 8

Preparation of 1-Decyne

The title compound was prepared according to Scheme 2 using the procedures of Example 1 and/or 2 starting from nonyl aldehyde. The title product was compared to an authentic reference, the yield is listed in Table 1.

Intermediate; 1,1-dichloro-1-decene

Yield: 98%. $^1$H-NMR $\delta(CDCl_3)$: 0.87 (t, 3H), 1.23–1.42 (m, 12H), 2.13–2.20 (m, 2H), 6.82 (t, 1H). $^{13}$C-NMR $\delta(CDCl_3)$: 14.00, 21.90, 22.12, 25.52, 29.87, 29.92, 31.82, 31.90, 121.3, 129.0 ppm. MS(CI/NH$_3$) (M+1): 210

EXAMPLE 9

Preparation of 3-Methyl-1-butyne

The title compound was prepared according to Scheme 2 using the procedures of Example 1 and/or 2 starting from isobutyraldehyde. The title product was compared to an authentic reference, the yield is listed in Table 1.

Intermediate; 1,1-dichloro-3-methyl-1-butene

Yield: 82%. $^1$H-NMR δ(CDCl$_3$): 0.92 (s, 3H), 0.99 (s, 3H), 1.59–1.70 (m, 1H), 4.25 (d, J=10.2 Hz, 1H). $^{13}$C-NMR δ(CDCl$_3$): 4.05, 5.32, 12.2, 72.02, 87.95 ppm. MS(CI/NH$_3$) (M+1): 140

TABLE 1

Compounds and Intermediates prepared by the Procedures of Scheme 2

Step 1

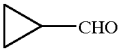

Step 2

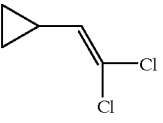

| Ex # | Aldehydes | Step 1 Dichloro-ethylenes | Yield (%)[a] | Step 2 Acetylenes | Yield (%)[a] |
|---|---|---|---|---|---|
| 2 | 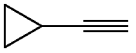 | 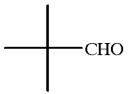 | 88 | 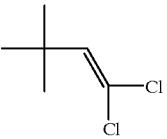 | 89 |
| 3 | 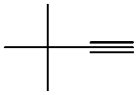 |  | 92[b] | 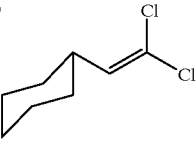 | 90 |
| 4 | 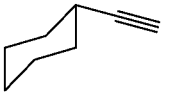 | 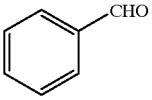 | 88 | 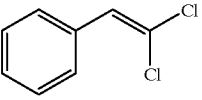 | 91[b] |
| 5 | 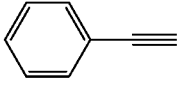 | 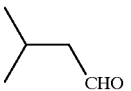 | 86 | 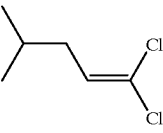 | 92 |
| 6 | 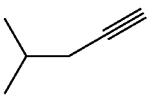 | 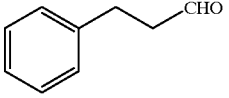 | 93 | 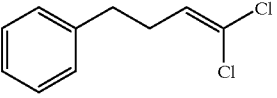 | 81[c] |
| 7 | 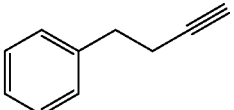 | | 85 | | 90[b] |

TABLE 1-continued

Compounds and Intermediates prepared by the Procedures of Scheme 2

| 8 | CH₃(CH₂)₇CHO | ![structure] CH₃(CH₂)₇ / C=CCl₂ | 95 | CH₃(CH₂)₇—≡≡≡ | 93[b] |
| 9 | iPr-CHO | iPr-CH=CCl₂ | 89 | iPr-≡≡≡ | 82 |

[a]Distilled material otherwise indicated.
[b]Crude yield
[c]Solution yield

What is claimed is:

1. A process for the preparation of a compound of formula (III);

$$R^1\text{—}\!\!\equiv\!\!\text{—}H \qquad (III)$$

wherein:
 R¹ is selected from:
  $C_{1-8}$ alkyl substituted with 0–3 R⁴,
  $C_{3-10}$ cycloalkyl substituted with 0–2 R⁵, and
  aryl substituted with 0–2 R⁶;
 R⁴, at each occurrence, is selected from methyl, ethyl, propyl, butyl, OR⁷, NR⁷R⁷ᵃ, phenyl, and cyclopropyl;
 R⁵, at each occurrence, is selected from D, methyl, ethyl, propyl, methoxy, ethoxy, and propoxy;
 R⁶, at each occurrence, is selected from methyl, ethyl, propyl, methoxy, ethoxy, propoxy, F, Cl, B, I, CN, and NR⁷R⁷ᵃ;
 R⁷ and R⁷ᵃ are independently selected from methyl, ethyl, propyl, and butyl;
said process comprising:
 (1a) reacting an aldehyde of formula R¹—CHO with trichloroacetic acid or tribromoacetic acid, in the presence of a base catalyst;
 (1b) reacting the solution of (1a) with zinc in the presence of an organic acid having one to six carbon atoms to form a compound of formula (II);

$$\begin{array}{c} R^1\diagdown \\ \phantom{R^1}\diagup\!\!\text{C}=\text{C}\diagdown\!\!R^2 \\ \phantom{R^1\diagdown\!\!\text{C}=\text{C}}R^2 \end{array} \qquad (II)$$

wherein R² is Cl or Br; and
 (2) reacting a compound of formula (II) with a strong base to form a compound of formula (III).

2. The process of claim 1 for the preparation of cyclopropylacetylene, said process comprising:
 (1a) reacting cyclopropane carboxaldehyde with trichloroacetic acid in the presence of a base catalyst;
 (1b) reacting the solution of (1a) with zinc in the presence of an organic acid having one to six carbon atoms to form 1,1-dichloro-2-cyclopropylethene; and
 (2) reacting 1,1-dichloro-2-cyclopropylethene with a strong base to form cyclopropyl acetylene.

3. The process of claim 2 wherein the base catalyst comprises sodium trichloroacetate.

4. The process of claim 2 wherein the organic acid comprises acetic acid.

5. The process of claim 2 wherein the strong base comprises methyl lithium or sodium amide.

6. The process of claim 2 comprising:
 (1a) reacting cyclopropane carboxaldehyde with trichloroacetic acid in the presence of a sodium trichloroacetate;
 (1b) reacting the solution of (1a) with zinc in the presence of acetic acid to form 1,1-dichloro-2-cyclopropylethene; and
 (2) reacting 1,1-dichloro-2-cyclopropylethene with methyl lithium to form cyclopropyl acetylene.

7. A process for the preparation of 1,1-dichloro-2-cyclopropylethene, said process comprising:
 (1a) reacting cyclopropane carboxaldehyde with trichloroacetic acid in the presence of a base catalyst; and
 (1b) reacting the solution of (1a) with zinc in the presence of an organic acid having one to six carbon atoms to form 1,1-dichloro-2-cyclopropylethene.

8. The process of claim 7 wherein the base catalyst comprises sodium trichloroacetate.

9. The process of claim 7 wherein the organic acid comprises acetic acid.

10. The process of claim 7 comprising:
 (1a) reacting cyclopropane carboxaldehyde with trichloroacetic acid in the presence of a sodium trichloroacetate; and
 (1b) reacting the solution of (1a) with zinc in the presence of acetic acid to form 1,1-dichloro-2-cyclopropylethene.

11. A process for the preparation of a compound of formula (III);

$$R^1\text{—}\!\!\equiv\!\!\text{—}H \qquad (III)$$

wherein:
 R¹ is selected from:
  $C_{1-8}$ alkyl substituted with 0–3 R⁴,
  $C_{3-10}$ cycloalkyl substituted with 0–2 R⁵, and
  aryl substituted with 0–2 R⁶;

R⁴, at each occurrence, is selected from methyl, ethyl, propyl, butyl, $OR^7$, $NR^7R^{7a}$, phenyl, and cyclopropyl;

R⁵, at each occurrence, is selected from D, methyl, ethyl, propyl, methoxy, ethoxy, and propoxy;

R⁶, at each occurrence, is selected from methyl, ethyl, propyl, methoxy, ethoxy, propoxy, F, Cl, B, I, CN, and $NR^7R^{7a}$;

R⁷ and $R^{7a}$ are independently selected from methyl, ethyl, propyl, and butyl;

said process comprising:

(1a) reacting an aldehyde of formula R¹—CHO with trichloroacetic acid or tribromoacetic acid, in the presence of a base catalyst;

(1b) reacting the solution of (1a) with a hydroxy group protecting agent;

(1c) reacting the solution of (1b) with zinc in the presence of an organic acid having one to six carbon atoms to form a compound of formula (II);

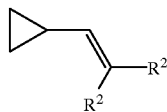

(II)

wherein R² is Cl or Br; and (2) reacting a compound of formula (II) with a strong base to form a compound of formula (III).

12. The process of claim 11 for the preparation of cyclopropylacetylene, said process comprising:

(1a) reacting cyclopropane carboxaldehyde with trichloroacetic acid in the presence of a base catalyst;

(1b) reacting the solution of (1a) with a hydroxy group protecting agent;

(1c) reacting the solution of (1b) with zinc in the presence of an organic acid having one to six carbon atoms to form 1,1-dichloro-2-cyclopropylethene; and (2) reacting 1,1-dichloro-2-cyclopropylethene with a strong base to form cyclopropyl acetylene.

13. The process of claim 12 wherein the base catalyst comprises sodium trichloroacetate.

14. The process of claim 12 wherein the hydroxy group protecting agent comprises acetic anhydride.

15. The process of claim 12 wherein the organic acid comprises acetic acid.

16. The process of claim 12 wherein the strong base comprises methyl lithium or sodium amide.

17. The process of claim 12 comprising:

(1a) reacting cyclopropane carboxaldehyde with trichloroacetic acid in the presence of sodium trichloroacetate;

(1b) reacting the solution of (1a) with acetic anhydride;

(1c) reacting the solution of (1b) with zinc in the presence of acetic acid to form 1,1-dichloro-2-cyclopropylethene; and (2) reacting 1,1-dichloro-2-cyclopropylethene with a methyl lithium to form cyclopropyl acetylene.

18. A process for the preparation of 1,1-dichloro-2-cyclopropylethene, said process comprising:

(1a) reacting cyclopropane carboxaldehyde with trichloroacetic acid in the presence of a base catalyst;

(1b) reacting the solution of (1a) with a hydroxy group protecting agent; and (1c) reacting the solution of (1b) with zinc in the presence of an organic acid having one to six carbon atoms to form 1,1-dichloro-2-cyclopropylethene.

19. The process of claim 18 wherein the base catalyst comprises sodium trichloroacetate.

20. The process of claim 18 wherein the hydroxy group protecting agent comprises acetic anhydride.

21. The process or claim 18 wherein the organic acid comprises acetic acid.

22. The process of claim 18 comprising:

(1a) reacting cyclopropane carboxaldehyde with trichloroacetic acid in the presence of sodium trichloroacetate;

(1b) reacting the solution of (1a) with acetic anhydride; and (1c) reacting the solution of (1b) with zinc in the presence of acetic acid to form 1,1-dichloro-2-cyclopropylethene.

* * * * *